(12) United States Patent
Baylatry et al.

(10) Patent No.: US 8,673,264 B2
(45) Date of Patent: Mar. 18, 2014

(54) INJECTABLE BIOMATERIAL

(75) Inventors: Minh Tam Baylatry, Paris (FR); Anouk Bisdorf-Bresson, Paris (FR); Denis Labarre, Villebon sur Yvette (FR); Alexandre Laurent, Courbevoie (FR); Laurence Moine, Saint Cloud (FR); Jean-Pierre Saint-Maurice, Arcueil (FR); Khelil Slimani, Le Plessis Robinson (FR); Michel Wassef, Paris (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 13/254,617

(22) PCT Filed: Mar. 2, 2010

(86) PCT No.: PCT/IB2010/000693
§ 371 (c)(1),
(2), (4) Date: Apr. 19, 2012

(87) PCT Pub. No.: WO2010/100564
PCT Pub. Date: Sep. 10, 2010

(65) Prior Publication Data
US 2012/0195826 A1    Aug. 2, 2012

Related U.S. Application Data

(60) Provisional application No. 61/156,737, filed on Mar. 2, 2009.

(51) Int. Cl.
*A61K 51/00* (2006.01)
*A61K 9/00* (2006.01)
*A61K 38/00* (2006.01)
*A61K 47/30* (2006.01)

(52) U.S. Cl.
USPC ......... 424/1.11; 424/400; 514/1.1; 514/772.3

(58) Field of Classification Search
None
See application file for complete search history.

(56) References Cited

U.S. PATENT DOCUMENTS

| | | |
|---|---|---|
| 2003/0211165 A1 | 11/2003 | Vogel et al. |
| 2005/0131458 A1 | 6/2005 | Batich et al. |
| 2005/0260276 A1 | 11/2005 | Yang et al. |
| 2006/0210635 A1 | 9/2006 | Laurent et al. |
| 2007/0031504 A1 | 2/2007 | Lien et al. |
| 2007/0299043 A1 * | 12/2007 | Hunter et al. .............. 514/171 |
| 2008/0220077 A1 | 9/2008 | Vogel et al. |
| 2010/0015195 A1 | 1/2010 | Jain et al. |
| 2010/0086602 A1 | 4/2010 | Egashira |
| 2010/0098735 A1 | 4/2010 | Jain et al. |
| 2010/0266491 A1 | 10/2010 | Farokhzad et al. |

FOREIGN PATENT DOCUMENTS

| | | | |
|---|---|---|---|
| EP | 2 057 987 | 5/2009 | |
| WO | 01 72281 | 10/2001 | |
| WO | 2004 069294 | 8/2004 | |
| WO | 2005 013810 | 2/2005 | |
| WO | 2007 014445 | 2/2007 | |
| WO | 2008 041245 | 4/2008 | |
| WO | WO 2008041245 A2 * | 4/2008 | ............... A61K 9/16 |
| WO | 2008 105773 | 9/2008 | |

OTHER PUBLICATIONS

International Search Report Issued May 30, 2011 in PCT/IB10/000693 filed Mar. 2, 2010.

* cited by examiner

*Primary Examiner* — Michael G Hartley
*Assistant Examiner* — Sun Y Kim
(74) *Attorney, Agent, or Firm* — Oblon, Spivak, McClelland, Maier & Neustadt, L.L.P.

(57) ABSTRACT

An injectable biomaterial containing a non-aqueous solvent suitable for injection to a human being and nanoparticles made of a polymer that is insoluble in water and insoluble in the non-aqueous solvent, in which the nanoparticles are loaded with a drug or a biological agent. The injectable biomaterial is suitable for occluding normal or malformative blood vessels or non-circulating cavities, or for necrosing tumors.

6 Claims, No Drawings

INJECTABLE BIOMATERIAL

The invention relates to an injectable biomaterial.

It also relates to kits of parts for reconstituting this injectable biomaterial.

Many injectable biomaterials are known for occluding vessels or non circulating cavities, or to necrose tumors.

For example, some organic solvents such as ethanol are injected in human body to induce locally a thrombosis, necrosis or sclerosis.

But, because such solvents diffuse very quickly in tissues, they have a limited efficacy on long term.

Furthermore, the application time of such a solvent in the target zone is too short so that these solvents are not effective.

Therefore, it has been proposed to use injectable solutions comprising not only an organic solvent but also a polymer. Such injectable solutions induce the formation of an implant and a local biological change due to the action of the solvent.

In these injectable solutions, the polymer is dissolved in a water miscible solvent and the obtained solution is injected in the body by means of a catheter or a needle, for example, and forms in situ a condensate (precipitate) when the solvent separates from the polymer and diffuses in the aqueous phase of the organism (blood, interstitial fluid, . . . ).

Such injectable solutions are in particular, commercialised under the tradename Onyx®, sold by the Company Micro-Therapeutics and Sclerogel® sold by the Company Gelscom.

It has also been proposed, in European Patent Application no. 1 581 274, to add microparticles to the injectable solutions comprising a solvent and a polymer in order to increase the final volume of the precipitate (condensate) which is formed.

In these three components solutions, the solvent is chosen among N-methylpyrrolidone, dimethylethylamide, diethylene glycol dimethyl ether, ethyl lactate, ethanol, dimethoxyethane, glycofurol, and mixtures thereof.

These three components solutions are used in particular to occlude arterial or venous vessels.

The three components solutions described above may also contain one or several drug(s) or biological agent(s) which is (are) to be delivered in situ. In such a case they are said to be "loaded" with a drug or a biological agent.

Such drugs are, for example, anti-inflammatory agents, angiogenic agents, antimitotics, angiogenesis inhibitors, growth factors, vitamins, hormones, proteins, vaccines, peptides, antiseptics and antimicrobial agents.

But when such solutions are used for the embolisation they may have a limited efficacy on long term due to recanalisation, i.e. the creation of by-passing vessels, and angiogenesis, i.e. the formation of new vessels which arises after the embolisation.

Such recanalisation and angiogenesis decrease the effectiveness of the occlusion.

The loading of the solvent or polymeric solution with drugs or biological agents enable to prevent these recanalisation and angiogenesis.

However, the release rate of the drugs or biological agents depends on the diffusion of the drug through the precipitate which is formed in situ.

Moreover, some drugs are partially or totally inactivated by the solvent present in the solution.

The present invention aims to palliate the limitation of the injectable solutions of the prior art.

For this aim, the invention proposes to encapsulate, or otherwise incorporate, the drugs or biological agents, in nanoparticles in order to protect the drugs or biological agents from an inactivation by the solvent and to make it possible to obtain a controlled and/or sustained (prolonged) release of the drugs or the biological agents.

Thus, according to a first embodiment and in its simplest form, the invention proposes an injectable biomaterial comprising:
 a non aqueous solvent which is injectable to human being,
 nanoparticles made of a polymer which is insoluble water and insoluble in the solvent cited above, and loaded with a drug or biological agent.

The solvent is a non aqueous solvent injectable to human being such as N-methylpyrrolidone, dimethylethylamide, diethylene glycol dimethyl ether, ethyl lactate, ethanol, dimethoxyethane, dimethylsulfoxide, glycofurol, and mixtures thereof.

Preferably the solvent is ethanol.

By loaded it is meant in the invention, that the drug or the biological agent is coated with, embedded with, or contained into, the nanoparticles.

By nanoparticles, it is meant in the invention, particles having at least two dimensions lower than 1 µm. Preferably, the nanoparticles are nanospheres or nanocapsules having an average size lower than 1 µm when measured by light scattering.

The nanoparticles may have an aqueous core or a matricial core.

When the nanoparticles have an aqueous core, they are used to contain an hydrophilic drug or biological agent.

In this case, the incorporation of the drugs or the biological agents in the nanocapsules is realized during the preparation of the nanoparticules which are themselves prepared by the double emulsion method. Such a method is disclosed in Tobio, M., R. Gref, A. Sanchez, R. Langer and M. J. Alonso (1998), "Stealth PLA-PEG nanoparticles as protein carriers for nasal administration." Pharm Res 15(2): 270-5 and Perez, C., A. Sanchez, D. Putnam, D. Ting, R. Langer and M. J. Alonso (2001), "Poly(lactic acid)-poly(ethylene glycol) nanoparticles as new carriers for the delivery of plasmid DNA," J Control Release 75(1-2): 211-24, Couvreur P, Barratt G, Fattal E, Legrand P, Vauthier C « Nanocapsule technology: a review». Crit Rev Ther Drug Carrier Syst. 2002; 19(2):99-134, for example.

When the drug or biological agent is water-insoluble, it is preferably incorporated in a nanosphere with a matricial core.

In that case, the incorporation of the drug or biological agent is made during the preparation of the nanoparticles themselves. The nanoparticles are prepared according to known methods such as the one described by Vauthier C, Bouchemal K "Methods for the preparation and manufacture of polymeric nanoparticles" Pharm Res 2009 May; 26(5): 1025-58.

The nanoparticle is made of a polymer which is insoluble in solvent commonly used in a solution injectable in human being, which is insoluble in water, which is suspendable in water miscible solvents, optionally by using a surfactant, and which is not degraded in the solvent.

Preferably, no diffusion of the solvent occurs through the polymer from which the nanoparticles are made.

The polymer from which the nanoparticles are made is preferably chosen among, polylactic acid (polylactide), polyglycolic acid (polyglycolide), lactide-glycolide copolymers, lactide-glycolide-polyethyleneglycol copolymers, polyorthoesters, polyanhydrides, poly(esters), poly(butyrolactone), poly(valerolactone), poly(malic acid) and generally polylactones and the copolymers of each of one or more of these polymers.

Preferably, the nanoparticles are made of lactide-glycolide-polyethyleneglycol copolymers.

These polymers form nanoparticles which contain, or coat the drug, or in which the drug is embedded, thus delaying the release of the drug.

It is to be noted that when the drug is sensitive to organic solvent, the nanoparticles furthermore protect the drug.

With the injectable biomaterial of the invention, the release or delivery of the drug or biological compounds is controlled and the release is sustained and prolonged during weeks or months until all the drug has diffused from the nanoparticles.

Thus, it clearly appears that the nanoparticles insure a protection of the drug or of the biological compound from a possible degradation or inactivation by the solvent of the injectable biomaterial of the invention by a mechanism of polymer shrinkage resulting in a pore closure, or by a mechanism of barrier protective effect between the core of the nanoparticles and the external solvent.

The release of the drug or the biological compound may occur following different mechanisms: a mechanism of diffusion of the drug or biological agent through the polymer and/or the pore of this polymer, constituting the nanoparticles, or a mechanism of hydrolysis of the nanoparticles, when the polymer from which they are made is resorbable in human body.

Any drug or biological agents may be incorporated in the nanoparticles but, preferably, the drug is an antibiotic, or a peptide, or a non-steroidal anti-inflammatory drug (NSAID), or an antiangiogenic drug.

When different drugs are to be incorporated in the injectable biomaterial, the nanoparticles may contain, individually, several types of pharmaceutically active compound but one can also prepare an injectable biomaterial containing nanoparticles containing one drug and a nanoparticle containing another drug, etc. . . .

In a second embodiment, the injectable biomaterial of the invention comprises not only the solvent and the nanoparticles in which a drug or a biological agent has been incorporated, but also a polymer. Such a polymer may be a poly (ethylene-co-vinyl-alcohol) copolymer (EVAL) or ethylcellulose, as in the prior art solutions, in particular the solutions Onyx® and Sclerogel®.

But, this polymer is preferably a linear polymer that is water-insoluble and soluble in the solvent in which the nanoparticles are suspended.

The linear polymers are preferably chosen from neutral or relatively uncharged polymers. Among such polymers, mention may in particular be made of poly(alkyl acrylates), poly (alkyl methacrylates), poly(alkyl cyanoacrylates), poly(vinyl acetates), poly(vinyl butyrates), poly(vinyl formals), poly(vinyl acetals), poly(vinyl butyrals), polyoxypropylenes, polyoxytetramethylenes, water-insoluble cellulose esters, water-insoluble esters of chitosan or other polysaccharides, poly (maleic acid) esters, poly(fumaric acid) esters, and water-insoluble linear copolymers or derivatives comprising these compounds.

Among these polymers, mention may most particularly be made of poly(hydroxyethyl methacrylate) (p(HEMA)), poly (methyl methacrylate) (PMMA), poly(hydroxypropyl methacrylate) (p(HPMA)), copolymers of hydroxyethyl methacrylate or hydroxypropyl methacrylate and of hexyl methacrylate (HEMA-HMA or HPMA-HMA), copolymers of hydroxyethyl methacrylate or hydroxypropyl methacrylate and of N-tert-butylacrylamide (HEMA-TBA or HPMA-TBA), copolymers of hydroxyethyl methacrylate or hydroxypropyl methacrylate and of acetoacetoxyethyl methacrylate (HEMA-AAMA or HPMA-AAMA), poly(N-acryloyl-2-amino-2-hydroxymethyl-1,3-propanediol) such as the product sold under the trade name Trisacryl(TRIS) by the company Biosepra (France), poly(n-2-hydroxypropyl methacrylamide), and derivatives thereof.

According to a preferred embodiment of the invention, the linear polymers are chosen among copolymers of hydroxypropyl methacrylate and of hexyl methacrylate (HPMA-HMA) and copolymers of hydroxypropyl methacrylate and of N-tert-butylacrylamide (HPMA-TBA).

This second embodiment is particularly preferred because the nanoparticles loaded with a drug are entrapped in the network of the gel formed by this polymer, in particular the linear polymer, and the release of the drug is even more delayed and controllable.

Indeed, the polymer forms in situ a condensate which precipitates, forming a gel and thus induces the formation of an implant.

But, in a third embodiment, the injectable biomaterial of the invention comprises not only, the solvent, the nanoparticles, the drug or biological agent and the polymer, preferably at least one linear polymer that is water-insoluble and soluble in the solvent, but also:
  at least one water-insoluble, hydrophilic cross-linked polymer, said cross-linked polymer having an affinity for said linear polymer, said hydrophilic cross-linked polymer being under the form of a suspension of particles in the solvent.

In this embodiment, due to the presence of the particles of hydrophilic cross-linked polymer, the cohesion of the gel formed with the at least one (linear) polymer is improved: the gel precipitates more quickly, is less deformable, delaying even more the release of the drug loaded in the nanoparticles.

Furthermore, the particles of the hydrophilic cross-linked polymer can be used as carrier for the nanoparticles loaded with the drug. Otherwise stated, the nanoparticles loaded with the drug can be "loaded" onto or into the microparticles of the hydrophilic cross-linked polymer.

Consequently, there are two variants of the injectable biomaterial oh the invention in its third embodiment:
1) The microparticles of the hydrophilic cross-linked polymer are added in a suspension containing the nanoparticles loaded with a drug or biological agent and the (linear) polymer: in that case the nanoparticles are not loaded onto the microparticles of the hydrophilic cross-linked polymer, and
2) The microparticles of the hydrophilic cross-linked polymer are poured in the suspension of nanoparticles loaded with the drug in water and the obtained suspension is freeze-dried. At this step, the nanoparticles are loaded onto or into the microparticles of the hydrophilic cross-linked polymer. Then the obtained freeze-dried solid particles are swelled in a solution of the (linear) polymer in the non aqueous solvent of the injectable biomaterial of the invention.

The hydrophilic cross-linked polymer, i.e. the polymer which is under the form of a microparticle, i.e. a particle having an average size, when measured by light scattering, higher than 10 μm, can be chosen among the polymers derived from the crosslinking of water-soluble linear polymers, such as alginates; starch derivatives; cellulose ethers; cellulose acetates with a degree of substitution of between 0.6 and 0.8; cellulose sulfates; water-soluble polysaccharides such as dextrans; chitosan salts; acrylic and methacrylic polymers; substituted or unsubstituted polyacrylamides and polymethacrylamides; hydrolyzed derivatives of poly(vinyl acetates), such as poly(vinyl alcohols); polymers derived from polyoxyethylene, polyethyleneimine; soluble salts of polyvinylpyridine; polyvinylpyrrolidone; polyurethanes; salts thereof and copolymers thereof.

Among the hydrophilic cross-linked polymers, mention may most particularly be made of the cross-linked polymers of HEMA, of HPMA, of acrylic acid or of poly(N-acryloyl-2-amino-2-hydroxymethyl-1,3-propanediol), and also the cross-linked copolymers of HEMA and of poly(N-acryloyl-2-amino-2-hydroxymethyl-1,3-propanediol), or of HPMA and of poly(N-acryloyl-2-amino-2-hydroxymethyl-1,3-propane-diol), and also the cross-linked copolymers of HEMA, of acrylic acid and of poly(N-acryloyl-2-amino-2-hydroxymethyl-1,3-propanediol), or of HPMA, of acrylic acid and of poly(N-acryloyl-2-amino-2-hydroxymethyl-1,3-propane-diol).

The cross-linking of the polymers can be carried out conventionally according to any method known to those skilled in the art, using a cross-linking agent such as, for example, methylenebisacrylamide.

The weight percentage of cross-linking agent, on the basis of the volume of the monomers from which the cross-linked polymer is obtained, is preferably between 0.5 and 12% (m/V), and even more preferably between 1 and 5% (m/V).

The hydrophilic cross-linked polymer for use in the present invention is under the form of solid particles.

Preferably, the solid particles of the hydrophilic cross-linked polymer are spherical in shape.

But, they may have any shape.

Hydrophilic cross-linked polymers for use in the present invention may have diameters ranging between about 10 μm to about 1000 μm and preferably between 20 and 100 μm and this represents the preferred variant of the third embodiment of the invention.

The injectable biomaterial of the invention, in all of its forms, preferably comprises from 0.1 to 20% m/V, preferably from 0.1 to 10% m/V inclusive of nanoparticles loaded with the drug.

The most preferably, the injectable biomaterial of the invention, in all its form, comprises from 1 to 10% m/V inclusive of nanoparticles loaded with a drug.

In the above percentages, V represents the total volume of the injectable biomaterial, including the nanoparticles.

Preferred embodiments of the injectable biomaterial of the invention are given below:

1. Nanocapsules for Delivery of an Antiangiogenic Monoclonal Antibody
    Solvent: ethanol,
    Nanoparticles: nanocapsules made of poly(ethylene glycol)-poly(lactide-coglycolide) (PEG-PLGA),
    Linear polymer: hydroxypropyl methacrylate-hexyl methacrylate copolymer (HPMA-HMA),
    Microparticles: cross-linked polymer: hydroxyethyl methacrylate/acrylic acid/N-acryloyl-2-amino-2-hydroxymethyl-1,3-propane-diol (HEMA/AA/TRIS) copolymer, and
    Pharmaceutically active ingredient: drug: Bevacizumab (Avastin®).

2. Nanoparticles: Nanospheres for Delivery of an Antiangiogenic Tyrosine Kinase Inhibitor
    Solvent: ethanol,
    Nanospheres made of a poly(ethyleneglycol)-poly(lactide-coglycolide) (PEG-PLGA) copolymer,
    Linear copolymer: hydroxypropyl methacrylate/hexyl methacrylate copolymer (HPMA-HMA),
    Microparticles: cross-linked polymer: (HEMA/AA/TRIS) copolymer, and
    Pharmaceutically active ingredient: drug: Sunitinib® (Sutent®).

3. Nanoparticles: Nanospheres for Delivery of an Antiangiogenic Metalloprotease Inhibitor
    Solvent: ethanol,
    Nanospheres made of a copolymer of PEG-PLGA,
    Linear copolymer: hydroxypropyl methacrylate/hexyl methacrylate copolymer (HPMA-HMA),
    Microparticles: cross-linked copolymer: (HEMA/AA/TRIS) copolymer, and
    Pharmaceutically active ingredient: drug: Prinomastat®.

When the injectable biomaterial of the invention furthermore comprises at least one polymer, then it is also called an injectable gel-forming composition.

In the preferred embodiment of the invention, the injectable biomaterial of the invention comprises microparticles of a cross-linked polymer which preferably represent from 1 to 25% (V/V) of the injectable gel-forming composition in accordance with the invention, and even more preferably from 5 to 12% (V/V).

As to the linear polymer, preferably, it represents from 3 to 30% (m/V) of the injectable gel-forming composition in accordance with the invention, and more preferably from 5 to 25% (m/V).

To prepare the injectable biomaterial of the invention, the nanoparticles loaded with the drug are:
1—either separated from the solvent used for their manufacture:
    by lyophilisation, optionally in presence of a cryoprotector, for example when the drug or biological agent with which they are loaded is hydrophobic and/or not temperature sensitive, or
    by centrifugation,
2—or left in the solvent used for their manufacture.

In the first case, the lyophilized or centrifuged nanoparticles are poured in the non aqueous solvent, at the desired concentration, and then the (linear) polymer and/or the microparticles of cross-linked polymer are poured in this suspension of nanoparticles.

In the second case, the microparticles of cross-linked polymer are directly poured in the suspension of nanoparticles and the mixture is freeze-dried. The obtained freeze-dried microparticles of cross-linked polymer loaded with the nanoparticles, themselves loaded with a drug or biological agent, are then poured in the non aqueous solvent of the injectable biomaterial of the invention already containing the (linear) polymer.

But the (linear) polymer may also be added in the non aqueous solvent after or together the freeze-dried loaded microparticles of hydrophilic cross-linked polymer loaded with the nanoparticles loaded with the drug or biological agent.

The injectable biomaterial of the invention may be prepared in advance and stored for later use. But it may also be prepared just before use, which permits to adapt it to the condition and subject to be treated by adjusting the amount of nanoparticles, the drug(s) or biological agent(s) they contain etc. . . .

Therefore, the invention also proposes kits of parts enabling to prepare the injectable biomaterial of the invention just before use.

The kit of parts for preparing the injectable biomaterial of the invention, in its simplest form, comprises dried nanoparticules loaded with a known concentration of a specific and known drug and a leaflet comprising instructions for reconstitution of the injectable biomaterial of the invention, and in particular for obtaining the correct and desired drug or biological agent concentration to be injected.

The kit of parts according to the invention can also comprise, in addition to the dried nanoparticules loaded with a known concentration of a known drug or biological agent, the (linear) polymer. The linear polymer can be in dry state or already in the non aqueous solvent to be used for the injectable biomaterial of the invention.

In a third embodiment, the kit of parts of the invention furthermore comprises the dried nanoparticles loaded with a known concentration of a known drug, the (linear) polymer and solid microparticles of the hydrophilic cross-linked polymer. The linear polymer can be in dry state or already in the non aqueous solvent to be used for the injectable biomaterial of the invention.

But, in a fourth embodiment, the kit of parts of the invention comprises, in addition to the (linear) polymer and the leaflet, nanoparticles loaded with the desired drug of biological agent, which are themselves "loaded" in or to the microparticles of a hydrophilic cross-linked polymer in the desired concentration. Otherwise stated, in this embodiment, the loaded nanoparticles are absorbed onto or entrapped into or otherwise bounded to the microparticles of hydrophilic cross-linked polymer.

With the kit of parts of the invention, the user can choose the amount of the different constituent of the injectable biomaterial to be injected. Otherwise stated, he can manufactured an injectable biomaterial containing the desired concentration of nanoparticles, microparticles, (linear) polymer, in the non aqueous solvent.

Thus, by selecting a particular concentration in nanoparticles, the user will select a particular quantity of drug or biological agent that he will injected.

The kit of parts of the invention can also contain a radio-opacifiant, preferably tantale.

It can furthermore contain a cryoprotector as example sucrose, maltose, trehalose, glucose, mannitol, sorbitol, polyols, albumin, PEG (poly(ethylene glycol), PVA (poly(vinyl alcohol), PVP, block copolymers based on ethylene oxide and propylene oxide, such as commercialised under the trademark Pluronic®, and poloxamers.

Preferably, the amount of dried linear polymer, in the kit of parts of the invention, is sufficient to obtain an injectable biomaterial containing from 5 to 25% m/V, inclusive, of dried polymer in the injectable biomaterial.

The amount of solid microspheres of hydrophilic cross-linked polymer, when present in the kit of parts of the invention, is also sufficient for obtaining concentration of solid microspheres of hydrophilic cross-linked polymer from 5 to 25% m/V, inclusive, in the injectable biomaterial.

The biomaterial of the invention may be particularly appropriate for occluding normal or malformative blood vessels and/or non circulating cavities in human body or for the sclerosis of tumor.

Therefore, the invention also proposes a method for occluding blood vessels and/or non circulatory cavities of human body or for necrosing tumor, comprising a step of invention in said blood vessels, or non circulating cavities, or tumor, of an injectable biomaterial according to the invention.

In order that the invention be better understood, none limitative and purely illustrative examples of embodiments thereof are given below.

EXAMPLE 1

Synthesis of Microspheres of Hydrophilic Cross-Linked Polymer: Synthesis of Microspheres of HEMA-TRIS-AA Cross-Linked with MBA An organic phase consisting of a solution of sorbitan oleate (Span 80®) (0.75 g) and sorbitan laurate (Span 20®) (0.45 g) dissolved in 300 ml of paraffin oil was introduced into a 2000 ml reactor and allowed to stand under a nitrogen atmosphere for 15 min. The monomer phase containing acrylic acid neutralized at 75% AA (0.78 g), hydroxyethyl methacrylate HEMA (7.23 g), Trisacryl TRIS (9 g), methylenebisacrylamide MBA (0.33 g) and 1 wt % ammonium peroxyde disulfate (0.6 g) solubilized in 60 ml of water was degassed by bubbling nitrogen through the solution for 15 min. The monomer phase was added to the organic phase at 90° C. and agitated by means of a propeller type stirrer at a velocity such as monomer droplets of the desired diameter are obtained. After 15 min, N,N,N',N'-tetramethylethylenediamine TEMED (0.15 g) were added. The suspension was stirred for 2 h at 70° C. The mixture was filtered hot and washed with water and acetone. Then, beads were freeze dried.

Size=28.5±1.7 µm (Particles size analyses were performed with a laser granulometer (Coulter LS 230, Beckman Coulter, Fullerton, USA).)

EXAMPLE 2

Synthesis of Linear Polymers: HPMA/HMA Copolymers

Appropriate amounts of HPMA and HMA were dissolved in 60 ml of ethanol into which 0.3 mol % AIBN with respect to monomers was added. The mixture was degassed with nitrogen and then heated at 80° C. for 4 h. Copolymers with various feed ratio of HPMA/tBA (100/0, 85/15, 70/30, 55/45 and 0/100) were prepared. The obtained copolymer was purified by precipitation in distilled water and dried under vacuum at 50° C. for 24 h.

Molecular mass and molecular weight distribution were determined by size exclusion chromatography (SEC). The composition of the copolymer was determined by $^1$H NMR.

Following table 1 summarizes the results of these analyses.

TABLE 1

| Reference | Ratio HMA/HPMA (mol/mol) | Mw (g/mol) | Ip* |
| --- | --- | --- | --- |
| CL-HMA-10 | 50/50 | 67 800 | 2.2 |
| CL-HMA-7 | 45/55 | 68 100 | 2.4 |
| CL-HMA-3 | 45/55 | 75 900 | 2.1 |
| CL-HMA-6 | 45/55 | 87 200 | 2.2 |
| CL-HMA-8 | 45/55 | 125 700 | 2.1 |
| CL-HMA-1 | 45/55 | 186 500 | 1.9 |
| CL-HMA-5 | 30/70 | 70 500 | 2.0 |
| CL-HMA-4 | 30/70 | 99 700 | 2.2 |
| CL-HMA-9 | 30/70 | 119 900 | 2.1 |
| CL-HMA-11 | 30/70 | 148 700 | 2.0 |
| CL-HMA-4b | 30/70 | 146 900 | 2.1 |

*Ip = polydispersity index

EXAMPLE 3

Preparation of Nanoparticles Loaded with an Antiangiogenic Tyrosine Kinase Inhibitor: Sunitinib®

In this example, two methods for preparing the loaded nanoparticles have been tested: with and without a surfactant.

Without surfactant:

Commercial PEG-PLGA (RESOMER® PEG Sample: Type RGP d 50-55, Diblock, 5% PEG with 5,000 Dalton, Boehringer Ingelheim Pharma GmbH & Co. KG) (50 mg) and Sunitinib® (610 µg) were dissolved in DMSO (2 ml). The organic phase was added dropwize into the aqueous phase (4 ml) under gentle stirring. Solvent and non-encapsulated Sunitinib® were removed by dialysis and then the nanoparticles were isolated from possible aggregates by centrifugation (5000 rpm, 10 min at 4° C.).
Size=161.8±7.1 nm (measured with a photon correlation spectroscopy (Zetasier Nano ZS, Malvern Instruments).
yield=weight of polymer incorporated in NP/weight of initial polymer=85%

With surfactant:
The same commercial PEG-PLGA as used in example 3 (5 mg) and a specified quantity of Sunitinib® were dissolved in DMSO (2 ml). The organic phase was added under gentle stirring into the aqueous phase (4 ml) containing Pluronic F68 (0.7% w/v). Solvent and non-encapsulated Sunitinib® were removed by dialysis and then the nanoparticles were isolated from possible aggregates by centrifugation (5000 rpm, 10 min at 4° C.).
Size=80±4.4 nm

EXAMPLE 4

Efficiency of the Encapsulation of Sunitinib®

The freeze-dried Sunitinib® loaded-nanoparticles were dissolved in DMSO (3 ml) (a common solvent for PEG-PLGA and the drug). Afterwards, Sunitinib® was assayed by spectrophotometry (430 nm).
The results are the following:
Without surfactant:
Encapsulation efficiency=PA final/PA initial× 100=20.6±6.1% in weight
With surfactant:
The encapsulation efficiency has been deteimined as a function of the initial weight of Sunitinib®.
The results are given in following table 2:

TABLE 2

| Initial weight of Sunitinib ® (μg) | Weight of Sunitinib ® "loaded" in the nanoparticles (μg) | Encapsulation efficiency (%) |
|---|---|---|
| 400 | 35 | 8 |
| 600 | 45 | 7 |
| 800 | 42 | 5 |
| 1000 | 36 | 3.5 |

EXAMPLE 5

Preparation of Nanocapsules Loaded with an Antiangiogenic Monoclonal Antibody: Avastin®

Avastin®-loaded PLGA nanoparticles were prepared using the solvent evaporation process involved the formation of double emulsion (w/o/w). 100 μl of an aqueous phase composed of Avastin® (500 μg) was emulsified in 1 ml of methylene chloride solution containing the same commercial PEG-PLGA as used in example 3 and 4 (50 mg) by sonication (30%, 1 min, Branson digital Sonifier) in an ice bath to form a primary w/o emulsion. Then, 2 ml of 3% (w/v) aqueous PVA solution was added to the emulsion and the mixture was re-emulsified by sonication (30%, 1 min) in ice bath. The resulting secondary w/o/w emulsion was then poured into 100 ml of a 0.3% (w/v) aqueous PVA solution under vigorous agitation to remove organic solvent for 1 h. The solution was filtered through bottle top filter with pore size of 0.45 μm and the filtrate was ultracentrifuged at 21,000 rpm for 20 min at 4° C. to isolate nanocapsule, followed by washing several times with distilled water and lyophilizing.
Size=263.7±4 nm

EXAMPLE 6

Efficiency of Encapsulation of Avastin®

The amount of Avastin® entrapped within PEG-PLGA nanocapsules was determined by the hydrolysis technique. Freeze-dried Avastin® loaded-nanocapsules (5 mg) were incubated in 5 ml of 0.1 N NaOH at room temperature until the complete dissolution of the nanocapsules. Afterwards, Avastin® was assayed by spectrophotometry (290 nm).
Encapsulation efficiency=56.0±5.6% in weight

EXAMPLE 7

Determination of the In Vitro Release of Sunitinib® from Nanoparticles

The study was performed on nanoparticles prepared according example 4 without surfactant.
In phosphate buffer saline (PBS):
Release of Sunitinib® from nanoparticles was conducted in PBS at 37° C. over a period of 24 h. The nanosuspension was directly divided in 1 ml sample after dialysis. 1 ml of PBS (0.02M) was added in each vial to obtain a PBS solution of 0.01M. At specified time, three sample solutions were taken out and filtered through the ultrafiltration membrane (Amicon® with a molecular weight cut off point at 30 000 Da) by centrifugation (12 500 rpm, 30 min). The supernatants were used for the HPLC analysis. The HPLC conditions were: column SGE HPLC Wakosil C18 RS; column temperature: 40° C.; mobile phase: acrylonitrile/phosphate buffer: 39/61 (pH 3.2); flow rate: 1 ml/min; wavelength: 431 nm.
After 24 hours, 10 wt % of the initial weight of Sunitinib® introduced in the nanoparticles are released.

EXAMPLE 8

Preparation of the Microspheres of the Cross-Linked Hydrophilic Polymer HEMA-TRIS-AA Loaded with the Nanoparticles Themselves Loaded with Sunitinib®, without Cryoprotector The nanoparticles loaded with Sunitinib® and in suspension in water, from example 3, (40 mg of nanoparticles, 10 ml) were directly added after dialysis onto dried HEMA-TRIS-AA microspheres (0.3 g). After swelling of the microspheres by the nanosuspension, the mixture was freeze-dried.
Characterizations:
The microspheres of the cross-linked hydrophilic polymer HEMA-TRIS-AA alone in water and the microspheres of the cross-linked hydrophilic polymer HEMA-TRIS-AA containing the nanoparticles in water have been observed by optical microscopy.
The optical microscopy shows that there is no aggregation of the microspheres of the cross-linked hydrophilic polymer due to the loading with the nanoparticles.
The two suspensions were also analyzed by granulometry.
The granulometry results show that the loading of the nanoparticles on or into the microspheres does not change the size and the distribution of size of the microspheres.

EXAMPLE 9

Preparation of the Microspheres of the Cross-Linked Hydrophilic Polymer HEMA-TRIS-AA Loaded with the Nanoparticles Themselves Loaded with Sunitinib®, with Cryoprotector The nanoparticles loaded with Sunitinib® from example 3 (40 mg of nanoparticles, 10 ml) were freeze-dried after dialysis in presence of a cryoprotector (PVA 0.2% w/v). The dried loaded nanoparticles were suspended in water (10 ml) and added onto dried HEMA-TRIS-AA microspheres (0.3 g). After swelling of the microspheres by the nano suspension, the mixture was freeze-dried.

EXAMPLE 10

Control of the Release of Nanoparticles from the Microspheres

The aim of this example is to check that the nanoparticles loaded with a drug are not released in the solvent of the suspension to be injected and released in water medium after injection.

1) Release of nanoparticles in ethanol as solvent:

0.1 g HEMA-TRIS-AA microspheres loaded with nanoparticles, themselves loaded with a drug, prepared according example 9 were suspended in ethanol (4 ml). At specified time, the suspension was centrifuged. The supernatant was taken out and analyzed by photon correlation spectroscopy (Zetasier Nano ZS, Malvern Instruments). Fresh ethanol was then added back to re-suspend the microspheres for the next time point. At t=0, 1 and 24 h, no nanoparticles has been detected in the supernatant showing that the nanoparticles were not released in ethanol.

2) Release of nanoparticles in water as solvent:

0.1 g HEMA-TRIS-AA microspheres loaded with nanoparticles, themselves loaded with a drug, prepared according example 8 were suspended in water (4 ml). At specified time, the suspension was centrifuged. The supernatant was taken out and analyzed by photon correlation spectroscopy (Zetasier Nano ZS, Malvern Instruments). Fresh water was then added back to re-suspend the microspheres for the next time point. At each time (t=0, 1 and 24 h), nanoparticles has been detected in the supernatant showing a progressive release of the nanoparticles in water.

EXAMPLE 11

This example shows that the viscosity of the injectable biomaterial of the invention is not changed as compared to the injectable biomaterial of the prior art: Occlugel®.

1.68 g (2% w/w) of HPMA/HMA copolymer (45/55; Mw: 88 000 g/mol) were dissolved in ethanol (2 ml). Then, microspheres loaded with nanoparticles loaded with Sunitinib®, obtained in example 9 (0.21 g, 10% (v/v)) and tantale (0.66 g, 33% w/w) (Tantalum metal powder: 1-5 μm (ATLANTIC EQUIP ENGINER, Bergenfield, N.J)) were added and stirred to form a homogeneous suspension.

Tantale is a radio opacifiant agent which is added in the biomaterial of the invention before its injection and which enables to visualise and follow, by imaging, the procedure of injection.

Indeed, the injectable gel forming compositions in accordance with the invention can also contain one or more adjuvants chosen from dyes (in order to make the composition visible when it is injected); imaging markers, such as contrast agents for X ray imaging, for instance iodinated products and metal powders, including tantalum and tungsten, or for ultrasound or MRI imaging, diagnostic or therapeutic.

Characterization:

Viscosity: The viscosity of the compositions was measured using a Hanke RheoStress(R) RS 600 controlled-stress rheometer sold by the company Rheo, Champlan, France. A plate/plate geometry was used. The protocol consisted of an increase in shear from 0 to 500 Pa over a period of two minutes at 20 [deg.] C.

Viscosity of Occlugel® (without nanoparticles)= 52.13±5.45 cP

Viscosity of the biomaterial of the invention prepared in example 12 (with nanoparticles)=50.04±6.02 cP.

The results above show that the viscosity of the injectable biomaterial of the invention is not change as compared to the one of the injectable biomaterial of the prior art Occlugel®.

EXAMPLE 12

In Vitro Release of Sunitinib from the Biomaterial of the Invention Prepared in Example 11

Release of Sunitinib® from the biomaterial of the invention prepared in example 11 was conducted in PBS at 37° C. over a period of 24 h. 1 ml of suspension prepared from example 11 was injected to 5 ml in PBS solution (0.01M). At particular time intervals, test samples of 1 ml were taken out and filtered through the ultrafiltration membrane (Amicon® with a molecular weight cut off point at 30 000 Da) by centrifugation (12 500 rpm, 30 min). Fresh PBS was then added back to refill the sample volume for the next time point. The supernatants were used for the HPLC analysis. The HPLC conditions were: column SGE HPLC Wakosil C18 RS; column temperature: 40° C.; mobile phase: acrylonitrile/phosphate buffer: 39/61(pH 3.2); flow rate: 1 ml/min; wavelength: 431 nm.

After 24 hours, 3 wt % of the initial weight of Sunitinib® introduced are released.

The results of the HPLC analysis show that the injectable biomaterial of the invention delay the release of the active ingredient as compared to an injectable biomaterial containing only nanoparticles (see example 7 above) of a polymer insoluble in water and insoluble in the non aqueous solvent and loaded with a drug.

The invention claimed is:

1. An injectable biomaterial comprising:
ethanol;
a nanoparticle comprising a polymer that is insoluble in water and insoluble in ethanol, in which the polymer is a lactide-glycolide-polyethyleneglycol copolymer;
a hydroxypropyl methacrylate-N-tert-butylacrylamide copolymer (HPMA-TBA);
a drug or a biological agent; and
a solid microparticle of a water-insoluble, hydrophilic cross-linked polymer which is a copolymer of hydroxyethyl methacrylate, poly(N-acryloyl-2-amino-2-hydroxymethyl-1,3-propanediol, and acrylic acid (HEMA-TRIS-AA) cross-linked with methylene bisacrylamide (MBA).

2. The injectable biomaterial of claim 1, wherein the drug or biological agent is selected from the group consisting of an antibiotic, a peptide, a non steroidal anti-inflammatory drug (NSAID), and an antiangiogenic drug.

3. The injectable biomaterial of claim 1, wherein the solid microparticle of the hydrophilic cross-linked polymer is a microsphere of from 10 μm to 1000 μm.

4. The injectable biomaterial according to claim 3, wherein a mean diameter of the solid microparticle of the hydrophilic cross-linked polymer is between 20 μm and 100 μm inclusive.

5. The injectable biomaterial of claim 1, wherein the nanoparticle has a concentration of from 0.1 to 20% m/V inclusive.

6. A therapeutic agent comprising the injectable biomaterial of claim 1,
wherein the drug or the biological agent causes necrosis of tumors.

\* \* \* \* \*